United States Patent [19]

Bornhorst et al.

[11] 3,976,080
[45] Aug. 24, 1976

[54] ENDOTRACHEAL TUBE HOLDER

[75] Inventors: Walter J. Bornhorst, Acton; Steven J. Coleman, Marlboro; James W. O'Brien, Waltham, all of Mass.

[73] Assignee: Thermo Electron Corporation, Waltham, Mass.

[22] Filed: Sept. 3, 1974

[21] Appl. No.: 502,692

[52] U.S. Cl. .......................... 128/348; 128/DIG. 26
[51] Int. Cl.² .................................... A61M 25/00
[58] Field of Search .................. 128/133, 206–208, 128/214 R, 215, 346–349 R, 350 R, 351, DIG. 6, DIG. 16, DIG. 26; 248/74 R, 74 A, 205 A, 74 B, 205 R; 24/73 SH, 73 SA, 73 AP, 81 CC

[56] References Cited
UNITED STATES PATENTS

| | | | |
|---|---|---|---|
| 2,606,555 | 8/1952 | Solomon | 128/171 |
| 2,820,457 | 1/1958 | Phillips | 128/351 |
| 2,908,269 | 10/1959 | Cheng | 128/351 |
| 3,046,989 | 7/1962 | Hill | 128/206 |
| 3,059,645 | 10/1962 | Hasbrouck et al. | 128/133 |
| 3,774,616 | 11/1973 | White et al. | 128/351 |

FOREIGN PATENTS OR APPLICATIONS

| | | | |
|---|---|---|---|
| 1,184,139 | 1959 | France | 128/348 |
| 653,436 | 1937 | Germany | 128/349 |
| 138,001 | 1961 | U.S.S.R. | 128/208 |

*Primary Examiner*—John D. Yasko
*Attorney, Agent, or Firm*—James L. Neal

[57] ABSTRACT

An endotracheal tube holder comprises a substantially straight projection having a laterally curved, trough-like surface mounted on a base for securing said projection to a person's head such that the projection is adapted to receive in longitudinally aligned relation the protruding end of an endotracheal tube in its applied working position. A pair of laterally opposed tabs at the outer end of the projection serve as stop lugs for preventing a wrapping, such as tape, which binds the tube to the projection from sliding off the projection.

4 Claims, 5 Drawing Figures

ENDOTRACHEAL TUBE HOLDER

CROSS-REFERENCE TO RELATED APPLICATION

The subject matter of this application is related to application Ser. No. 503,010, filed Sept. 3, 1974.

BACKGROUND OF THE INVENTION

The present invention relates generally to the art of positioning and securing an endotracheal tube for conducting air, oxygen or an oxygen and anesthetic gas mixture. It is well known to those skilled in the art that support means may be applied to the mouth to prevent axial and lateral movement of such an endotracheal tube. Such an oral endotracheal tube is generally referred to as an orotracheal tube. However, previous devices for that purpose leave much room for improvement. For example, some provide a method of attachment of the orotracheal tube to the support means which allows the tube to slip or causes the tube to become occluded by the pressure from the attachment means. Other devices cover the mouth, lips and surrounding area causing irritation to the skin and hindering adequate access to the oral cavity.

It is an object of the present invention to provide an endotracheal tube holder having means for attaching an endotracheal tube to it securely and easily and which prevents both axial and lateral movement of the tube relative to the trachea.

It is another object of the present invention to provide an orotracheal tube holder with integral bite blocks adapted to fit between a person's teeth to prevent him from biting down on the tube and occluding it and to preserve an opening through which to insert special purpose catheters into the mouth.

It is another object of this invention to provide an orotracheal tube holder which leaves the mouth, lips and surrounding skin substantially uncovered, thereby allowing visual monitoring of lip color and adequate access to the oral cavity while avoiding the damage to skin tissue which results from the skin being covered for long periods of time.

SUMMARY OF THE INVENTION

The invention described herein is an improved endotracheal tube holder having an elongated, shallow trough-like projection adapted to receive in longitudinally aligned relation to the outside surface of an endotracheal tube. The projection can be easily and securely attached to the tube by tape or other means. The projection has protruding tabs at its end to block the tape or other similar means so that it does not slide off. The projection is connected to means for mounting it on a person's head and is anchored thereby with sufficient strength to secure the tube.

A preferred embodiment of the invention comprises a plastic frame placed around the mouth for holding the projection in place near the center of the mouth in a position such that it may be attached to the protruding end of an orotracheal tube in its applied working position to prevent both axial and lateral movement of the tube.

DETAILED DESCRIPTION OF THE DRAWINGS

Figure 1:
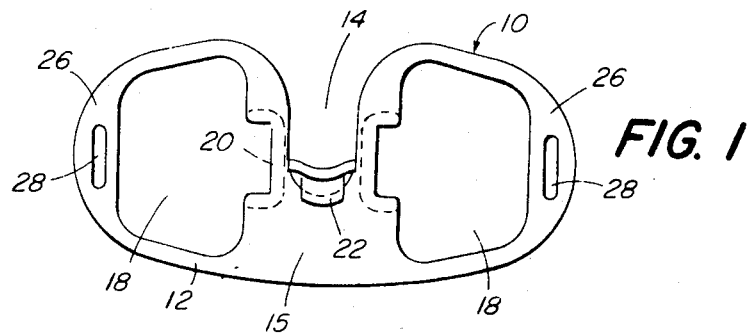
FIG. 1 is a frontal elevation of one embodiment of the present invention.
Figure 2:
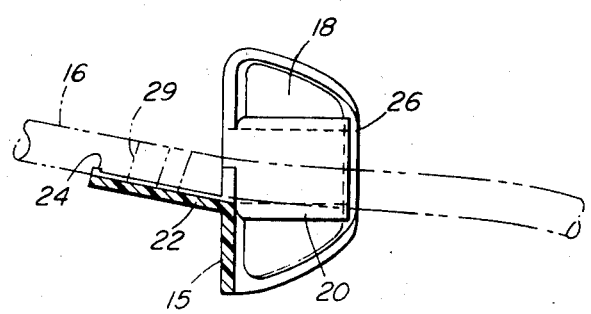
FIG. 2 is a cross section taken along a vertical center line of the invention shown in FIG. 1.
Figure 3:
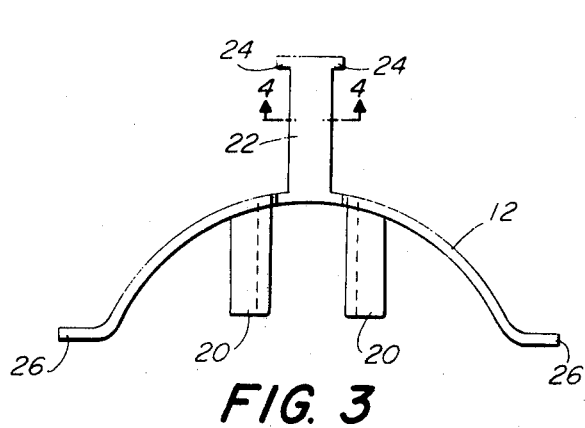
FIG. 3 is a plan view of the invention shown in FIG. 1.

Referring to FIGS. 1 - 3, a preferred embodiment of an endotracheal tube holder 10 for supporting an endotracheal tube has a base or frame 12 made of a suitable plastic material and is adapted to externally border the mouth. The frame 12 is in a generally oval shape, the upper portion of the oval being adapted to be seated over the upper lip, the lower portion under the lower lip, the plane of the oval being curved to conform to the contour of the face. The frame is indented to form a deep notch 14 in the center of the upper portion, said upper portion thus merging into the sides of the notch, and the sides of the notch join a solid piece 15 forming the lower center portion of the frame. The width and bottom curvature of the notch are such that it is adapted to receive an endotracheal tube 16 extending therethrough. The notch 14 and bridge-like solid piece 15 are positioned centrally within the frame, dividing the frame into two halves, each half forming two closed loops on either side of the notch. The loops bound two open areas 18 within the generally oval outline of the frame. When the tube holder is in its operative position the outer portion of the frame 12 surrounds the lips, the two open areas 18 are directly over the lips and mouth, and the notch 14 is positioned centrally over the mouth.

In FIG. 3 two bite blocks 20 are shown integrally formed with the frame and extending inwardly from the inside surface of the frame in parallel spaced relation on opposite sides of the notch. When the tube holder is in its applied working position the bite blocks project into the mouth between the teeth for preventing the mouth from closing and thus occluding the airway.

Figure 4:
FIG. 4 is a cross section of the device shown in FIG. 3 taken along line 4 — 4.

A salient feature of this invention best shown in FIGS. 2, 3 and 4 is an elongated projection 22, one end of which is integrally mounted on the solid bridge-like part 15 of the frame just beneath the notch and the other end of which has small opposing tabs 24 on each side. The projection is laterally curved along its length, thus forming a shallow trough. The curvature of the trough is similar to that of typical outside radii of endotracheal tubes to facilitate mounting of such a tube upon the projection. The projection is sufficiently narrow that the tube lays upon it as upon a supporting platform rather than mating with it as with a circumscribing sleeve or partial sleeve. The curve of the projection contacts the tube along an arc substantially less than 180° in extent. The projection extends substantially perpendicularly to the outer surface of the frame, angled slightly so that it leans toward the notch. The two opposing tabs 24 protrude from opposite sides of the projection at its outer end to serve as stop lugs.

The edges of the frame at the ends of the oval are slightly widened and curved away from the contour of the face at that point to form a small flange 26. Each flange has a slot 28 in it adapted to receive one end of a fastening strap, not shown.

In operation, after an endotracheal tube has been inserted orally by methods well known to those skilled in the art, the tube holder is positioned so that the tube rests in the notch 14, the bite blocks are between the teeth, and the frame is seated against the face. The bite blocks prevent the mouth from closing, thus ensuring a passageway into the oral cavity for other special purpose tubes. The side walls of the bite blocks are longer than the diameter of an endotracheal tube so they prevent the patient from occluding the tube with his teeth.

When the frame is firmly seated, a strap is inserted through the slots 28 in the ends of the frame, passed around the head and tightened. This anchors the tube holder firmly in place. An adjustable cloth strap is preferred to provide a firm attachment of the holder without the excessive pressure sometimes caused by an elastic strap.

The endotracheal tube is pressed to the bottom of the notch and axially aligned with the projection 22 mounted on the frame. Fastening means such as tape 29 is wrapped around both the projection and tube for binding them tightly together. Adhesive tape is one acceptable fastening means because it is commonly available in hospitals where a tracheal tube would be used and it offers a quick, convenient and inexpensive means of attachment. Moreover, it does not tend to close off the tube.

Figure 5:
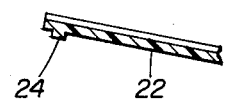
FIG. 5 is a cross section of an alternate embodiment of the device shown in FIG. 3 taken along line 5 — 5.

The danger of slippage is also greatly reduced because of the unique design of this tube holder. The tube holder is in close contact with the mouth, lips and tongue and it tends to become moist during use. Good securing contact between the fastening means and the projection tends to be difficult to achieve; the bond between the fastening means and the tube holder can loosen and cause the fastening means to slide off the holder. However, according to the present invention the fastening means cannot slide past the end of the projection. At that point the fastening means will engage the protruding tabs 24 and be stopped from any further movement. This, in turn, inhibits any further movement of the endotracheal tube. An alternate embodiment of the projection 22 is shown in FIG. 5. The tab means 24 extends downwards near the end of the projection.

The use of a frame with large open areas 18 is another important feature of this invention. One index used to determine a patient's condition is the color of his lips, and the open areas allow observation of the lips quite easily. Further, the open areas provide sufficient room for the insertion of suction catheters and any other necessary tube means into the oral cavity. Finally, the present tube holder with its open areas avoids covering large areas of the skin. This is important because prolonged coverage of the skin causes the tissue to become irritated and break down.

I claim:

1. A tube holder for securing an endotracheal tube in its applied working position comprising:

a generally oval frame adapted to border the outside of the mouth of a subject and conform to the contour of the face around the mouth leaving the mouth substantially uncovered, said frame having an upper portion which seats above the upper lip, a lower portion which seats below the lower lip, means in the central, upper portion of said frame forming a notch and a solid bridge-like structure beneath said notch, said notch being adapted to receive the protruding end of an endotracheal tube in its applied working position;

a single elongated substantially straight platform forming a surface laterally curved to form a shallow trough for receiving the outside surface of an endotracheal tube and adapted to receive an adhesive strip wrapped around both such tube and said platform to bind such tube securely to said platform, said platform being integrally formed with said frame and extending from said bridge-like member at the base of said notch for receiving the protruding end of an endotracheal tube in its applied working position, said platform forming an obtuse angle with said bridge-like member; and means adjacent the free end of said platform for preventing such adhesive strip from slipping off the free end of said platform.

2. A tube holder according to claim 1, wherein said means adjacent the end of said platform comprises a pair of opposed lugs.

3. The invention of claim 1, wherein said frame forms two open areas, one on each side of said notch.

4. The invention of claim 1, comprising means on each side of said frame adapted to receive an adjustable band for encircling the head to hold said frame securely on the face.

* * * * *